United States Patent [19]

Shin et al.

[11] Patent Number: 5,224,982
[45] Date of Patent: * Jul. 6, 1993

[54] METHODS AND COMPOSITIONS FOR TREATING PLANTS EXPOSED TO WATER DEPRIVATION STRESS

[75] Inventors: Charles C. Shin; Nicolai A. Favstritsky, both of Lafayette, Ind.

[73] Assignee: Great Lakes Chemical Corporation, W. Lafayette, Ind.

[*] Notice: The portion of the term of this patent subsequent to Mar. 2, 2009 has been disclaimed.

[21] Appl. No.: 846,377

[22] Filed: Mar. 6, 1992

[51] Int. Cl.$^5$ ............................................. A01N 43/08
[52] U.S. Cl. ............................... 504/294; 71/DIG. 1; 504/140
[58] Field of Search ............................................. 71/88

[56] References Cited

U.S. PATENT DOCUMENTS 4,615,725 10/1986 Weissmuller et al. ............... 71/88
4,886,543 12/1989 Shin et al. ............................... 71/88

Primary Examiner—Glennon H. Hollrah
Assistant Examiner—B. Bembenick
Attorney, Agent, or Firm—Woodard, Emhardt, Naughton, Moriarty & McNett

[57] ABSTRACT

Methods and compositions for the protection of plant tissue from damage upon exposure to certain environmental and handling stresses, and to assist plant tissue in recovering from environmental and handling stress injuries, include the application of an effective amount of stress-protectant compositions selected from the group consisting of tetrahydrofurfuryl alcohol, tetrahydrofurfuryl amine and mixtures thereof. The compositions are applied as aqueous solutions containing between about 0.005 and about 25 wt % of the stress-protectant components. Surfactants may be included to improve application of the compositions to the plant tissues.

24 Claims, No Drawings

METHODS AND COMPOSITIONS FOR TREATING PLANTS EXPOSED TO WATER DEPRIVATION STRESS

BACKGROUND OF THE INVENTION

1. Field of the Invention

The present invention relates to methods and compositions for the treatment of plants to reduce injury due to exposure to certain environmental and handling stresses, and more particularly to the application of compositions to plants to minimize or prevent stress injuries. The present invention further relates to the treatment of plants which have been subjected to injury due to exposure to the identified stresses.

2. Description of the Prior Art

Plants are subject to exposure to a variety of environmental and handling stresses. Forms of stress which can adversely affect plants include stresses due to water deprivation, drought and excessive heat. Adverse effects may also occur during the handling of plants or plant products, such as in transplanting, rooting cuttings, germinating seeds, and preserving cut flowers.

It is desirable to treat plants to avoid any detrimental affects that would otherwise result under these circumstances. In order to be practically useful, a chemical composition used to treat plants against these stress injuries must be non-toxic to the plants, environmentally acceptable and relatively inexpensive. The present invention satisfies these requirements and provides for the protection of plants from environmental and handling stresses of the types previously mentioned.

SUMMARY OF THE INVENTION

In accordance with this invention, there are provided methods and compositions for protecting plants and plant products from certain environmental and handling stresses, and for promoting recovery of plants from stress injuries. A plant anti-stress chemical composition has been discovered which comprises an aqueous solution containing an effective amount of a chemical component selected from the group of tetrahydrofurfuryl alcohol, tetrahydrofurfuryl amine, and mixtures thereof. The solution is applied to the plant surfaces and tissues prior to and/or after exposure to the stress. The solution preferably includes between about 0.005 and about 25 wt. % of the stress protectant.

Among the objects of this invention is the provision of compositions and methods to protect plants and plant products from damage due to certain environmental and handling stresses, e.g., those which occur in conjunction with excessive heat, water deprivation, drought, seed germination, transplanting, rooting cuttings and preserving cut flowers.

Another object is the provision of an effective method for treating plants and plant products injured due to exposure to such environmental and handling stresses.

A further object of this invention is to provide such stress protectant compositions and methods which are relatively inexpensive, non-toxic and environmentally acceptable.

These and other objects and features of this invention will be apparent from the description hereafter.

DESCRIPTION OF THE PREFERRED EMBODIMENTS

For the purposes of promoting an understanding of the principles of the invention, reference will now be made to the preferred embodiment of the invention and specific language will be used to describe the same. It will nevertheless be understood that modifications and further applications of the principles of the invention are contemplated as would normally occur to one skilled in the art to which the invention relates.

Exposure of plant tissue to a variety of environmental and handling stresses can result in serious damage. Many of these stresses are related to the amount of water available to the plant tissue, and the present invention is concerned in particular with stresses relating to this phenomenon. Such forms of environmental stress which can adversely affect plant tissue include stresses due to water deprivation (e.g., absence of rainfall, lack of irrigation, low humidity, etc.), drought and excessive heat. As used herein, the term "environmental stress" includes each of the foregoing forms of plant stress. Adverse effects may also occur through a similar mechanism during the handling of plants or plant products, such as in transplanting plants, rooting cuttings, germinating seeds, and preserving cut flowers. Plants and plant products are also subjected to related stress following harvesting and during subsequent transportation. As used herein, the term "handling stress" encompasses each of the foregoing forms of stress. The term "plant tissue" is used to indicate either plants or plant products subject to damage by exposure to the identified environmental or handling stresses. The present invention is not directed to the treatment of plants which have been exposed to chilling or freezing temperatures.

The extent and nature of damage resulting from exposure to the environmental and handling stresses is exemplified by the effect of water deprivation on plants. Water deprivation can reduce plant growth, resulting in lower weight gain of the plant, as well as reduced crop production. The damage is also exemplified by the effect on seed germination, with untreated seeds showing delayed and lower percentage germination. The impact of plant tissue treatments in regard to water deprivation and seed germination are appropriate and useful models for demonstrating the efficacy of compositions and methods on the protection of plant tissue from the water-related, environmental and handling stresses addressed by the present invention.

In accordance with this invention, a plant tissue, stress-protectant composition has been discovered which comprises an aqueous solution containing a stress-protectant component selected from the group consisting of tetrahydrofurfuryl alcohol, tetrahydrofurfuryl amine, and mixtures thereof. Preferably, the composition comprises an aqueous solution comprising between about 0.005 and about 25 wt. percent of the stress-protectant component, and most preferably comprises between about 0.05 and about 5 wt. percent of the stress-protectant component. It has also been discovered that the stress-protectant composition is effective in promoting a recovery of plant tissue from the environmental and handling stresses.

Tetrahydrofurfuryl alcohol is a colorless, high boiling, primary alcohol having the following structure:

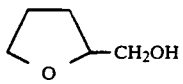

Tetrahydrofurfuryl amine is a colorless, high boiling, primary amine having the following structure:

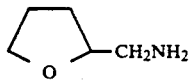

Both tetrahydrofurfuryl alcohol and tetrahydrofurfuryl amine exhibit stress-protectant properties as against exposure to the described water-related, environmental and handling stresses. However, tetrahydrofurfuryl alcohol is preferred in accordance with the present invention.

Tetrahydrofurfuryl alcohol (THFA) is produced by the hydrogenation of furfuryl alcohol. As expected on the basis of its structure, tetrahydrofurfuryl alcohol exhibits behavioral characteristics of both alcohol and ethers. Due to its cyclic ether structure, tetrahydrofurfuryl alcohol possesses distinctly unique solvent properties which are desirable. THFA is low in volatility (vapor pressure is 2.3 mm Hg at 39° C.), non-damaging and non-toxic, biodegradable, easily absorbable, able to penetrate membranes, considerably soluble in water, in addition to forming multiple hydrogen bonds, and able to dissolve electrolytes. Tetrahydrofurfuryl amine has similarly useful characteristics.

The resistance of plant tissues to the environmental and handling stresses is increased through the application of the stress-protectant compositions of this invention, such as by spraying or root trenching methods with respect to plants, or mixing or soaking for seeds. The composition is applied at moderate, ambient temperatures, i.e., at temperatures of the air surrounding the plant tissues above a chilling temperature. Any conventional apparatus suitable for aqueous solutions may be employed for the foregoing application methods. For spraying, the plant tissues to be treated are thoroughly sprayed so that all of the plant tissue surfaces are substantially covered. Due to the size, shape and/or other characteristics (such as surface properties) of a plant, an application may require two or more sprayings.

The compositions may be formulated and supplied to the user ready to apply, or in concentrated form and diluted to the desired strength prior to application to the plant tissues. No special handling or mixing steps are required. THFA and tetrahydrofurfuryl amine are stable in aqueous solution. Moreover, these compositions are stable to light and do not need to be stored in an opaque container nor prepared immediately prior to application.

Since aqueous THFA or tetrahydrofurfuryl amine solutions, or mixtures thereof, may not completely wet the surfaces of some plant tissues, such as leaves having waxy surfaces, it is preferred for some applications that the compositions include non-ionic surfactants. Suitable surfactants operate as penetrating agents and otherwise may be inert, or at least non-interfering, components. For example, two different surfactants, polyoxyethylene sorbitan monolaurate (Tween 20) and polyoxyethylene sorbitan monooleate (Tween 80) have been found to improve the effectiveness of the compositions in appropriate circumstances. When non-ionic surfactants are used, it is preferred that the stress-protectant composition contain between about 0.005 and about 0.5 wt. percent of the non-ionic surfactant.

The stress-protectant compositions of the present invention may be applied to the plant tissues from immediately prior to 24 hours prior to exposure to the stress conditions, and preferably at least about 4 or more preferably at least about 12 hours prior to exposure. For optimal results it is preferred that the stress-protectant compositions be repeatedly applied prior to exposure to the stress exposure. For additional protection, the stress-protectant compositions may be applied immediately after the stress exposure to help the plants or plant products recover from any stress injuries that are incurred. For maximum protection during extended periods of exposure to stress conditions, such as those brought on by severe drought or heat, it may be desirable to apply the stress-protectant compositions periodically, such as weekly.

As indicated, the stress compositions and methods of the present invention are applicable for the treatment of plant tissues, i.e., plants and plant products, exposed to a variety of environmental and handling stresses. These forms of stress are related by the fact that the stresses are manifested as a water-related effect. This explains the applicability of the stress-protectant compositions to a wide range of environmental and handling stresses, as well as types of plants and plant products.

The following examples serve to further illustrate the invention, with all percentages being by weight unless otherwise indicated. It will be appreciated that these examples are demonstrative only, and the applicability of the compositions and methods described therein extends to the various other plants and plant products, as well as the differing types of environmental and handling stresses, elsewhere described herein.

EXAMPLE 1

The efficacy of the present invention is readily demonstrated by the results of experiments showing reduction in plant injuries induced by water deprivation. A set of twenty-four pepper plants (c.v. MaBelle) with similar growth development (39 days old) was selected. The average height of the plant was 7.5 cm. In order to achieve uniform water status, each plant was watered with a fixed amount of DI water, 15 ml, for 16 days. At 55 days old, these peppers were then divided into four sets (6 plants per set). For each treatment, the first set received 15 ml of water, the second set received 5 ml of DI water, the third set received 5 ml of an aqueous mixture solution of 0.2% THFA and 0.1% Tween 20, and the fourth set received 5 ml of an aqueous solution of 0.5% THFA and 0.1% Tween 20. The treatment was repeated three times a week for 2 weeks and then normal watering was resumed as usual until harvest time. The harvest data of the tests are listed in Table 1, with the last column showing as a percent the number of plants which were lost as a result of the water deprivation stress. The results show that plants treated with an aqueous mixture solution of THFA and Tween 20 performed substantially better than the untreated plants.

TABLE 1

Harvest Results per 6 Water Stressed Pepper Plants

| Stress | Treatment | Total # of Peppers | Weight per Pepper | Total Weight | % Increase Weight | % Lost to Water Stress |
|---|---|---|---|---|---|---|
| Non-Stress Control | DI Water | 13 | 34.1 g | 443 g | 170% | 0 |
| 67% water w/held 2 wks | DI Water | 7 | 23.4 g | 164 g | — | 63 |
| 67% water w/held 2 wks | 0.2% THFA & 0.1% Tween 20 | 9 | 27.8 g | 250 g | 52% | 44 |
| 67% water w/held 2 wks | 0.5% THFA & 0.1% Tween 20 | 14 | 34.2 g | 479 g | 192% | 0 |

EXAMPLE 2

The experimental procedure for Example 1 was repeated. Fifteen bean plants each were treated in various ways and the stress-protectant agent was applied in two different application methods (spray and root drench). The results listed in Table 2 show that both spray and root drench applications are effective in alleviating injury of the bean plants from water deficiency. The bean plants treated with an aqueous solution of 0.5% THFA and 0.1% Tween 20 harvested as much as the non-treated, non-stressed bean plants. The effectiveness of root drench application indicates that if THFA is absorbed efficiently, THFA without surfactant Tween 20 is also effective in alleviating the injury of plants.

TABLE 2

Harvest Results per 15 Water Stressed Bean Plants

| Stress | Treatment | Total # of Pods | Weight per Pod | Total Harvest Weight | % Lost to Water Stress |
|---|---|---|---|---|---|
| Non-Stress Control | DI Water | 13 | 1.18 g | 15.4 g | 0 |
| 67% water w/held 2 wks | DI Water Foliage Spray | 6 | 0.8 g | 4.8 g | 69 |
| 67% water w/held 2 wks | 0.1% THFA & 0.1% Tween 20 Foliage Spray | 24 | 0.6 g | 13.8 g | 11 |
| 67% water w/held 2 wks | 0.5% THFA & 0.1% Tween 20 Foliage Spray | 20 | 0.8 g | 15.1 g | 2 |
| 67% water w/held 2 wks | DI Water Root Drench | 2 | 0.02 g | 0.04 g | 100 |
| 67% water w/held 2 wks | 0.1% THFA Root Drench | 14 | 0.7 g | 10.4 g | 32 |
| 67% water w/held 2 wks | 0.5% THFA Root Drench | 7 | 0.6 g | 4.2 g | 73 |

EXAMPLE 3

The experimental procedure in Example 1 was followed. Each set of 5 cucumber plants was treated with aqueous solutions of DI water, 1.0% THFA plus 0.1% Tween 20 for spraying, 1.0% THFA only for root drenching. The harvest results in Table 3 show both root drenching and leaf spraying of the agent saved approximately 30% of the crop otherwise lost to water deficiency.

TABLE 3

Harvest Results per 5 Water Stressed Cucumber Plants

| Stress | Treatment | Total Wt. of Harvest, g | % Increase Over Control | % Lost in Yield Due to Stress |
|---|---|---|---|---|
| 67% water w/held for 2 wks | DI water Root Drench | 2399 | — | 29 |
| 67% water w/held for 2 wks | 1.0% THFA Root Drench | 3057 | 24.7 | 8 |
| 67% water w/held for 2 wks | 0.1% THFA Root Drench | 2875 | 19.8 | 14 |
| 67% water w/held for 2 wks | DI Water Foliage Spray | 1939 | — | 42 |
| 67% water w/held for 2 wks | 1.0% THFA & 0.1% Tween 20 Foliage Spray | 2475 | 27.6 | 26 |
| 67% water w/held for 2 wks | 0.1% THFA & 0.1% Tween 20 Foliage Spray | 2974 | 53.4 | 11 |
| Non-Stress Control | DI water | 3338 | — | 0 |

EXAMPLE 4

A total of ninety-two bean plants with similar physical characteristics was transplanted into forty-six 8" plastic pots (two plants per pot). When the bean plants were 14 days old water conditioning began. It took 4 weeks to get a uniform water status before water deficiency became stressful. The first set of 23 pots was treated with an aqueous solution of THFA containing 0.25% of THFA and 0.1% Tween 20 surfactant. The second set of pots was treated with an aqueous solution of 0.1% Tween 20. The treated plants underwent water restriction for 40 days before regular greenhouse watering resumed. During this stress period the plants were treated once every seven days for five consecutive weeks. After 14 days of regular watering, the harvest results were collected as shown in Table 4. The bean plants treated with an aqueous mixture solution of 0.25% THFA and 0.1% Tween 20 produced 31% more fruit than the plants treated with an aqueous solution of 0.1% Tween 20. The average weight of pods for the treated plants was 21% greater than for the untreated plants.

TABLE 4

| Treatment | Harvest Results per 46 Water Stressed Bean Plants | | |
|---|---|---|---|
| | Total # of Pods | Total Yield, g | Avg. Wt. of Pod |
| 0.1% Tween 20 | 154 | 511.7 | 4.0 |
| 0.25% THFA & 0.1% Tween 20 | 166 | 669.6 | 3.3 |
| % Increase Over Control | 7.8% | 30.9% | 21.2% |

EXAMPLE 5

The test procedure in Example 5 was repeated. In this example, the stress period was shortened (21 days vs. 40 days stress). The harvest results are listed in Table 5. The test results indicate that if the bean plant receives more stress, the effectiveness of the treatment is greater.

TABLE 5

| Treatment | Harvest Results per 50 Water Stressed Bean Plants | | |
|---|---|---|---|
| | Total # of Pods | Total Yield, g | Avg. Wt. of Pod |
| 0.25% THFA & 0.1% Tween 20 | 99 | 361.5 g | 3.65 g |
| Control (0.1% Tween 20) | 90 | 326.3 g | 3.62 g |
| % Increase Over Control | 10.0% | 10.8% | 0.8% |

EXAMPLE 6

The efficacy of the present invention is also demonstrated by the results of experiments showing reduction in plant injuries induced at the time of seed germination. An annual loss of as much as 60 MM (in 1980 dollars) in the cotton industry reflects the economic impact of injuries incurred immediately following field planting. Other crops that suffer stand loss, delayed maturity, and reduced yield as a result of injuries following planting include soybean, lima bean, cucumbers, tomato, pepper, eggplant, okra, and various cereal crops. Experimental evidence leads to the conclusion that the seeds are particularly sensitive during initial hydration. The level of seed moisture determines sensitivity of the seed to injury during inhibition.

The cotton variety (Stoneville) was planted on Feb. 19, 1992 in 9 oz. plastic cups for germination evaluation. Prior to planting, twenty seeds each were imbibed in a 1% aqueous solution of THFA and DI water respectively, at $-1°$ C. for six hours. The seeds were germinated in an indoor greenhouse, under artificial fluorescent light, at 30° C. with the lights on. The light period was 14 hours on and 10 hours off. On Feb. 24, 1992, the emerged embryo were counted. The germination rate of the seed treated with THFA was 85% (17 emerged out of 20 seeds), compared with 35% (7 emerged out of 20 seeds) of DI water treated seed. The seed treated with aqueous THFA solution germinated earlier than the non-treated seed.

EXAMPLE 7

The sweet corn varieties (Sweetheart, Classic, and Champ) were planted on May 8, 1991 in four 40' rows. Prior to planting, half of each seed lot from Classic and Champ was imbibed with water and with the agent (0.8% THFA and 0.2% Tween 20) for 62 hours at 34° F. The night temperatures for 4 days preceding the planting date for corn were cold enough (minimum temperature 0.5° C. to 9.5° C.) to stress germination and emergence. Actual soil temperature on the May 8 planting date was about 10° C. in the top 10 cm of soil. The sweet corn was harvested on Jul. 30, 1991. The combined harvest of both sweet corn varieties treated with the chemical agent was 41% higher in ear number (116 vs. 82), and 56% greater in ear weight (64.5 vs. 41.8 lbs.) compared with the water treated check. The ears were also larger in the treated corn varieties than the non-treated checks.

EXAMPLE 8

The foregoing procedures are repeated for other stress-protectant compositions of the present invention. For example, the anti-stress agents include:

1. tetrahydrofurfuryl alcohol dissolved in deionized (DI) water to make 0.05% and 0.5% THFA aqueous solutions;

2. 0.1 parts of a surfactant, polyoxyethylene sorbitan monolaurate (Tween 20), and 0.05-0.5 parts tetrahydrofurfuryl alcohol dissolved in 99.4-99.85 parts DI water to make an aqueous 0.05-0.5% THFA+0.1% Tween 20 solution;

3. tetrahydrofurfuryl amine dissolved in DI water to make 0.3% tetrahydrofurfuryl amine aqueous solution;

4. 0.1 parts of a surfactant, Tween 20, and 0.3 parts of tetrahydrofurfuryl amine dissolved in 99.60 parts of DI water to make an aqueous 0.3% tetrahydrofurfuryl amine+0.1% Tween 20 solution; and 5. the foregoing solutions 2 and 4, except using Tween 80.

Application of the foregoing compositions to the plant tissues, prior to exposure to the environmental and handling stresses, provides protection against stress injuries. The treated plants display better growth than the untreated plants. Protection of the plants is also obtained upon treatment with aqueous solutions containing as low as 0.005 wt. % and as high as 25 wt. % of the tetrahydrofurfuryl amine, as well as mixtures of the alcohol and the amine yielding total weight percentages as indicated. Generally, treatments with the amine and mixtures of the amine and the alcohol give comparable results to treatments with the tetrahydrofurfuryl alcohol solutions alone. Treatment with Tween 20 or Tween 80 alone has no effect on protecting plants from environmental or handling stress injuries.

EXAMPLE 9

Treatment with the inventive compositions of plants which have already received stress injuries can also contribute to plant recovery and improved plant growth. Plants, injured from environmental and handling stress exposure, which are treated immediately following exposure to the injurious stresses, display better growth and development than untreated plants.

While the invention has been described in detail in the foregoing description and its specific Examples, the same is to be considered as illustrative and not restrictive in character. Only the preferred embodiments have been described, and all changes and modifications that come within the spirit of the invention are desired to be protected.

What is claimed is:

1. A method for increasing the resistance of plant tissue to damage upon exposure to water deprivation stress thereby reducing damage to plant tissue upon exposure to water deprivation stress which comprises applying to the plant tissue an effective amount of a water deprivation stress-protectant composition selected from the group consisting of tetrahydrofurfuryl alcohol, tetrahydrofurfuryl amine and mixtures thereof.

2. The method of claim 1 in which said applying comprises applying an aqueous solution of the stress-protectant composition.

3. The method of claim 2 in which the aqueous solution contains between 0.005 and 25 wt % of the stress-protectant composition.

4. The method of claim 3 in which the aqueous solution contains between 0.05 and 5.0 wt % of the stress-protectant composition.

5. The method of claim 2 in which the stress-protectant composition consists essentially of an aqueous solution of tetrahydrofurfuryl alcohol.

6. The method of claim 5 in which the aqueous solution contains between 0.05 and 5.0 wt % of the tetrahydrofurfuryl alcohol.

7. The method of claim 2 in which the aqueous solution further contains a non-ionic surfactant.

8. The method of claim 7 in which the aqueous solution contains between 0.05 and 0.5 wt % of the non-ionic surfactant.

9. The method of claim 7 in which the non-ionic surfactant is selected from the group consisting of polyoxyethylene sorbitan monolaurate and polyoxyethylene sorbitan monooleate.

10. The method of claim 1 for reducing damage to plant tissue upon seed germination.

11. The method of claim 1 in which said stress-protectant composition is applied a sufficient time prior to exposure to the stress to permit at least partial absorption of the composition by the plant tissue.

12. The method of claim 11 in which the stress-protectant composition is applied at least about 4 hours prior to exposure of the plant tissue to the stress.

13. The method of claim 11 in which the stress-protectant composition is applied at least about 12 hours prior to exposure of the plant tissue to the stress.

14. The method of claim 11 in which the stress-protectant composition is applied to the plant tissue at least twice prior to exposure of the plant tissue to the stress.

15. The method of claim 11 in which the stress-protectant composition is also applied to the plant tissue after exposure of the plant tissue to the stress.

16. A method for the treatment of plant tissue injured due to exposure to water deprivation stress which comprises applying to the plant tissue an effective amount of a water deprivation stress-recovery composition selected from the group consisting of tetrahydrofurfuryl alcohol, tetrahydrofurfuryl amine and mixtures thereof.

17. The method of claim 16 in which said applying comprises applying an aqueous solution of the stress-recovery composition.

18. The method of claim 17 in which the aqueous solution contains between 0.005 and 25 wt % of the stress-recovery composition.

19. The method of claim 18 in which the aqueous solution contains between 0.05 and 5.0 wt % of the stress-recovery composition.

20. The method of claim 19 in which the stress-recovery composition consists essentially of an aqueous solution of tetrahydrofurfuryl alcohol.

21. The method of claim 20 in which the aqueous solution contains between 0.05 and 5.0 wt % of the tetrahydrofurfuryl alcohol.

22. The method of claim 17 in which the aqueous solution further contains a non-ionic surfactant.

23. The method of claim 22 in which the aqueous solution contains between 0.05 and 0.5 wt % of the non-ionic surfactant.

24. The method of claim 22 in which the non-ionic surfactant is selected from the group consisting of polyoxyethylene sorbitan monolaurate and polyoxyethylene sorbitan monooleate.

* * * * *